United States Patent [19]

McMichael

[11] Patent Number: 4,705,685

[45] Date of Patent: Nov. 10, 1987

[54] METHODS AND MATERIALS FOR TREATMENT OF DISEASE STATES INVOLVING IMMUNOLOGICAL FACTORS

[76] Inventor: John McMichael, Cambridge Springs, Pa.

[21] Appl. No.: 708,274

[22] Filed: Mar. 5, 1985

Related U.S. Application Data

[62] Division of Ser. No. 378,752, May 17, 1982, Pat. No. 4,521,405.

[51] Int. Cl.$^4$ ............................................ A61K 39/165
[52] U.S. Cl. ...................................... 424/89; 424/93; 424/85
[58] Field of Search .............................. 424/88, 89, 93

[56] References Cited

U.S. PATENT DOCUMENTS 4,294,818 10/1981 McMichael et al. ................. 424/12

OTHER PUBLICATIONS

Chemical Abstracts, vol. 66, Abstract No. 9402a, 1967.
Permin, H., et al., Allergy, vol. 33, pp. 15-23, 1978.
European Journal of Chemical Investigation, vol. 10, No. 2, Apr. 1980, Abstract No. 81.
Holborow, et al., "Immunoassays in Autoimmune Disease", pp. 277-288 in *Immunoassays for the 80's*, Voller, et al., eds. (University Park Press, Baltimore, 1981).
Glossary in *Basic & Clinical Immunology*, Fudenberg, et al., eds. (Lange Medical Publications, Los Altos, California, 1980).

*Primary Examiner*—Blondel Hazel
*Attorney, Agent, or Firm*—Marshall, O'Toole, Gerstein, Murray & Bicknell

[57] ABSTRACT

In animals including humans, the symptoms of non-anaphylactic disease states wherein the disease victim's humoral and/or cell-mediated immunological response is involved in disease pathology are alleviated upon administration of compositions comprising mixtures of histamine and one or more immunogenic substances participative in the humoral or cell-mediated pathogenic response. In preferred embodiments, the compositions are administered in essentially minute, "neutralizing" doses. Illustratively, significant relief of symptoms of multiple sclerosis is achieved through parenteral (e.g., subcutaneous or sublingual) administration of mixtures of histamine and measles virus immunogen. For a majority of patients, from about $8.8 \times 10^{-6}$ to $5.5 \times 10^{-3}$ mg of histamine phosphate will provide an effective quantity of histamine to a unit dose of the mixture. Likewise, a unit does of the mixture will contain from about $2 \times 10^{-3}$ to about $4 \times 10^{-4}$ times the prescribed vaccination dose of a killed, attenuated measles virus vaccine strain. As another example, rheumatoid arthritis symptoms are alleviated by administration of histamine admixed with an immunoglobulin G immunogen which is provocative of in vivo rheumatoid factor production.

Other immune disorders (e.g., chronic pain and herpes simplex type II infections) are effectively treated with admixtures of histamine and appropriate immunogen(s).

7 Claims, No Drawings

METHODS AND MATERIALS FOR TREATMENT OF DISEASE STATES INVOLVING IMMUNOLOGICAL FACTORS

This is a division of application Ser. No. 378,752, filed May 17, 1982 now U.S. Pat. No. 4,521,405.

BACKGROUND

The present invention relates generally to the treatment of disease states involving immunological factors and more particularly to methods and materials for alleviation of symptoms of nonanaphylactic disorders wherein disease pathology results in whole or part from the victim's own humoral and/or cell-mediated immune response to one or more immunogenic substances.

Disease states involving immunological factors may be seen to broadly comprise (1) immunodeficiency diseases, and (2) disorders wherein tissue injury occurs as a result of a humoral or cell-mediated response to immunogens (e.g., antigens) of endogenous or exogenous origin. This latter group of immunological disorders is frequently referred to as involving immune "hypersensitivity", with the numerous disease states comprehended by the term classified according to four hypersensitivity "reaction" types.

Type I reactions (frequently referred to as anaphylactic, immediate-type, atopic, reagenic, or IgE-mediated hypersensitivity reactions) generally result from the release of pharmacologically active substances such as histamine, slow-reacting substance of anaphylaxis (SRS-A), and eosinophilic chemotactic factor (ECF) form IgE-sensitized basophils and mast cells after contact with a specific exogenous antigen. Disease states in which Type I reactions play a role include allergic extrinsic asthma, seasonal allergic rhinitis, systemic anaphylaxis, and the like.

Type II reactions (also referred to as cytotoxic, cytolytic complement-dependent or cell-stimulating hypersensitivity reactions) result when antibody reacts with antigenic components of cells or tissue elements or with an anitgen or hapten which has become intimately coupled to cells or tissue. Disease states with which Type II reactions are associated include autoimmune hemolytic anemia, erythroblastosis fetalis and Goodpasture's disease.

Type III reactions (also referred to as toxic complex, soluble complex, or immune complex hypersensitivity reactions) result from the deposition of soluble circulating antigen-antibody complexes in vessels or in tissues, with accompanying acute inflammatory reactions at the site of immune complex deposition. Prototypical Type III reaction disorders include Arthus reaction, serum sickness, systemic lupus erythematosis, and certain types of glomerulonephritis.

Type IV reactions (frequently called cellular, cell-mediated, delayed, or tuberculin-type hypersensitivity reactions) are caused by sensitized T-lymphocytes which result from contact with a specific antigen. Examples of diseases cited as involving Type IV reactions are contact dermatitis and allograft rejection.

Of particular interest in consideration of the present invention are those immunological disorders, especially prominant in humans, which are commonly referred to as "autoimmune" diseases. While the classification originated to distinguish immune disorders involving reaction against "self" or endogenous antigens from those involving reaction against exogenous antigens, significant controversy exists over the criteria for establishing a particular disease as autoimmune in origin. Autoantibodies can frequently be demonstrated in a large number of individuals who are free of autoimmune disease and autoimmune diseases such as rheumatic heart disease appear to involve, inter alia, cross-reactive immune responses to antigens of clearly exogenous origins (Streptococcus sp.). The designation of a particular disease as an autoimmune disorder is often subjectively based on (1) presence of some evidence of an antigen-antibody reaction including an endogenous antigenic substance, (2) judgement that the immunologic findings are not merely secondary to some other disease state, and (3) the lack of other identifiable causes for the disorder.

While autoimmune disorders are frequently associated with Type II hypersensitivity reactions, there exists evidence of involvement of Type III and Type IV reactions in some autoimmune diseases. Essentially as a matter of definition, immunological disorders of the "anaphylactic" or IgE-mediated type (i.e., Type I hypersensitivity reactions) are not classified as autoimmune due to the clear involvement of clearly exogenous antigenic substances.

Autoimmune diseases are frequently characterized by means of their involvement of single organ or single cell-types or involvement of multiple organs or tissue systems. (Due to the frequent involvement of either connective tissue and blood vessels in the diseases of the latter, systemic, type, these have frequently been referred to as "collagen," or "collagen-vascular" or "connective tissue" diseases.)

Diseases frequently designated as single organ or single cell-type autoimmune disorders include: Hashimoto's thyroiditis, autommimune hemolytic anemia, autoimmune atrophic gastritis of pernicious anemia, autoimmune encephalomyelitis, autoimmune orchitis, Goopasture's disease, autoimmune thrombocytopenia, sympathetic ophthalmia, myasthenia gravis, Grave's disease, primary biliary cirrhosis, chronic aggressive hepatitis, ulcerative colitis and membranous glomerulopathy. Diseases often designated as involving systemic autoimmune disorder include: systemic lupus erythematosis, rheumatoid arthritis, Sjögren's syndrome, Reiter's syndrome, polymyositisdermatomyositis, systemic sclerosis, polyarteritis nodosa and multiple sclerosis.

It is unfortunately the case that the treatment of many of the above-noted autoimmune disorders is, at best, primitive and seldom effective in alleviating disease symptoms for significant periods of time. Progressive degenerative autoimmune diseases such as systemic lupus erythematosis, systemic sclerosis, polyarteritis, polymyositis and multiple sclerosis are usually treated by administration of high doses of corticosteroids to alleviate discomfort due to inflamation of tissues. Immunosuppressant therapy has proven to be of little value. Drug therapy (see, e.g., U.S. Pat. Nos. 3,864,481 and 4,113,858) has provided no consistent alleviation of the frequently painful symptoms nor altered substantially the general prognosis of progressive debilitation and death.

The following somewhat disparate items of information concerning the state of the art in immunology are of considerable interest to the background of the invention.

Histamine [4—(2-aminoethyl)—imidazole or β-imidazolyl-ethylamine] is a chemical substance possessing pronounced biological activities. It is a powerful stimulant of gastric secretion and constrictor of smooth muscle. It is a vasodilator and large doses cause a relatively rapid fall in blood pressure. It is frequently noted to be liberated by epithelial cells upon traumatic injury or stimulation by antigenic substances. Its storage in and release from mast cells and basophil granules and its role in Type I hypersensitivity reactions have been the subject of extensive study. At present, its clinical use is principally as a stimulant in diagnosis of impairment of gastric secretion. From time to time, therapeutic uses have been proposed including administration for alleviation of certain kinds of headache symptoms. With the single exception of an experimental study into use of homeopathic doses in treatment of multiple sclerosis [Jonez, "My Fight to Conquer Multiple Sclerosis," Messner (1952)] it has not been employed in the treatment of any autoimmune disorders.

To the extent that autoimmune diseases have been the subject of etiological investigation, it has frequently been the case that, with varying degrees of precision, one or more endogenous or exogenous immunogens has been associated with participation in formation of circulating antibodies. See, e.g., Holborow, et al., "Immunoassays in Autoimmune Disease" appearing at pp. 277-288 in "Immunossays for the 80's," Voller, et al., eds., University Park Press, Baltimore (1981). Results of such studies have been principally of diagnostic significance and have been of little use in formulating therapeutic regimens for the diseased patients. As one example, there have been numerous reports of isolation of circulating (humoral) antiviral antibodies from multiple sclerosis patients, including antibodies against vaccinia, rubella, herpes simplex, varicella-zoster, mumps, Epstein-Barr virus, adenovirus and even canine distemper virus. Despite the lack of any evidence of viral particle involvement in lesions or cerebrospinal fluids of mulitple sclerosis patients, one of the most consistently reported antiviral antibodies found in such patients has been antimeasles virus antibody. Further, the applicant and his co-workers were able to employ homogenized lymphocytes of multiple sclerosis patients to provoke formation of heterologous species antibodies which, in turn, have been found to be exceptionally useful in the development of diagnostic procedures. See, e.g., U.S. Pat. No. 4,294,818. This lymphocyte-associated immunogen, (i.e., the antigen responsible for formation of the highly specific antibodies reactive with sera of all multiple sclerosis patients) has not yet been purified to homogeneity and characterized, nor has it been employed in any form in any known therapeutic regimen for alleviation of multiple sclerosis symptoms. As another example, the rheumatoid arthritis disease state is frequently proposed as having an autoimmune basis on the ground of a characteristic presence of circulating "RF" (rheumatoid factor), an anti-immunoglobulin antibody directed at IgG. In seropositive patients, it is proposed that RF, which can undergo a complement fixing interaction with IgG is involved in inducing and maintaining chronic synovitis.

Finally, over the last twenty or so years, a small body of information has developed concernng a therapeutic regimen known as "provocative neutralization" therapy. See, e.g., Miller, "Food Allergy, Provocative Testing and Injection Therapy," Charles C. Thomas, Springfield, Ill. (1972); Miller, *Annals of Allergy*, 38, pp. 185-191 (1977); Miller, *Trans.Am.Soc.Opth.&Otolar.Allergy*, 14, pp. 159-168 (1974); and Miller, *Clinical Med.*, 81, pp. 16-19 (1974). Briefly put, the therapeutic scheme involves subcutaneous administration of a known "causative" agent of a particular disease state in amounts comprising the patient's maximum tolerated intradermal dose. This dose is defined as the smallest dilution (i.e., highest concentration) of the substance which will produce a negative wheel when employed in a standard skin test injection procedure. The proposed mode of operation of this regimen is through modulation of subpopulations of T-lymphocytes. Initial successes for this treatment procedure were reported in the context of relief of headache symptoms correlated with food allergies. Subsequently, relief of symptoms of acute influenza infection has been reported to attend provocative neutralization treatments with live attenuated influenza virus. Further, relief from herpes simplex Type I infection has been reported for patients treated with influenza virus.

BRIEF SUMMARY

Provided by the present invention are novel methods and materials for obtaining signifcant alleviation of symptoms of nonanaphylactic disease states wherein tissue injury results from the disease victim's own humoral and/or cell-mediated immunological response to one or more immunogenic substances of endogenous or exogenous origin. Compositions administered according to the invention comprise mixtures of histamine and one or more of the immunogenic substances specifically immunologically associated with the disease state (as indicated by, e.g., characteristic elevation of circulating antibodies thereto in the disease victim). The compositions are administered in small, "neutralizing" doses. The mixtures may be provided in any immunologically acceptable diluent, with or without immunological adjuvants.

As examples of the practice of the invention, a study of the effects of administration of a histamine phosphate and measles virus mixture to a large number of multiple sclerosis patients has revealed remarkably high percentages of patients reporting substantial improvement in disease symptoms. Rheumatoid arthritis patients treated according to the invention with compositions including histamine and, for example, rabbit anti-sheep red blood cell immunoglobulin G (IgG) which is provocative of rheumatoid factor (RF) formation in humans have uniformly reported relief of arthritis symptoms.

According to another aspect of the invention, relief of disease state symptoms has been achieved with respect to disorders not classically described as directly involving immunological factors. As an example, patients experiencing chronic pain of a duration of three months or more (having a history of either osteoarthritis or major physical trauma) have all reported relief of pain upon treatment with mixtures of histamine and inactivated, attenuated measles virus. In a like manner, patients experiencing recurrent herpes simplex virus type II infection have reported relief of lesion pain and lesion enlargement upon treatment with compositions including histamine, measles inactivated, attenuated virus and influenza vaccine (killed) virus.

The histamine component of mixtures prepared according to the present invention is suitably provided in the form of a water soluble histamine salt. The presently preferred form of histamine is histamine phosphate. For a majority of patients, from about $8.8 \times 10^{-6}$ to $5.5 \times 10^{-3}$ mg and preferably $4.4 \times 10^{-5}$ to $1.1 \times 10^{-3}$ mg of histamine phosphate will be effective.

Expectedly, the immunogen components of mixtures may be provided in forms of varying purity or homogeneity. As one example, measles virus immunogen may be provided to mixtures of the invention in the force of a inactivated, attenuated measles virus vaccine or as an immunologically active measles virus fraction (e.g., surface antigen preparation) derived from such inactivated, attenuated vaccine strains of virus. Mixtures including histamines and from about $2 \times 10^{-3}$ to about $4 \times 10^{-4}$ times the prescribed vaccination dose of killed, attenuated measles virus have been found to be quite useful. In a like manner, the mixture employed in treatment of rheumatoid arthritis may include Immunoglobulin G as described above or, e.g., the so-called "antigenic," FC region of the heavy IgG chain or a synthetic replica thereof. Mixtures including from 0.1 to 0.005 mg of chromatographically pure IgG have proven to be useful.

Positive therapeutic results to date have attended the administration of histamine and immunogen as mixture components, but have not been noted when these substances were individually administered, indicating a type of synergistic, joint activity or formation of a histamine/immunogen complex which can act as a regulatory molecule for gene expression. This is consistent with the regulatory activity of other well-defined low molecular weight substances.

One route of parenteral administration practiced according to the invention is the subcutaneous injection of the compositions. Alternately, the compositions may be administered sublingually with good results. Pharmaceutically acceptable diluents, adjuvants and carriers may suitably be employed.

Other aspects and advantages of the present invention will be apparent upon consideration of the following detailed description of illustrative examples of the practice thereof.

DETAILED DESCRIPTION

According to the present invention novel compositions are provided which comprise mixtures of histamine and one or more immunogens. These compositions, in turn, are useful as therapeutic agents in the alleviation of the symptoms of disorders wherein the disease victim's own humoral and/or cell-mediated immunological response is involved in the disease pathology.

Histamine employed in the present invention is preferably provided in the form of a water solubule histamine salt such as histamine phosphate, salicylate, dihydrochloride, or the like. A suitable histamine source for use in formulating mixtures of the invention is available from Eli Lilly as "Histamine Phosphate Injection, U.S.P." which is provided in 5 ml units, each ml containing 0.55 mg of histamine phosphate (equivalent to 0.2 mg histamine base) with 16 mg glycerin and 2 mg phenol.

As employed herein with respect to mixture components of the invention, "immunogen" shall be defined as a substance which, upon introduction into an animal, is capable of stimulating an immune response. As such, the term includes, but is not limited to, "anitgens" which combine with antibodies and/or provoke formation of antibodies in the animal.

One or more immunogens may be provided to mixtures of the invention in forms of widely varying purity or homogeneity. Where the immunogen employed is of viral origin, for example, it may be provided in the form of whole, inactivated virus particles. Expectedly, much preferred forms of live viruses are attenuated strains commonly employed as non-disease-producing but nonetheless immunogenic vaccine components. Further, wherever possible, isolated immunogenic fragments of viruses or viral fragment replicas (such as surface antigen isolates or replicas thereof) would be most preferred unless it is established that viral RNA or DNA provides the principal immunogen of interest. As another example, where the immunogen of interest is an antigen which is a constituent of an antibody substance (e.g., an antigenic portion of an immunoglobulin) it may be provided as a pure antigenic isolate from the antibody, or a synthetic replica of such an antigen, or in the form of the "whole" antibody.

Selection of one or more immunogens for incorporation into a mixture with histamine is made in the context of "specific immunological association" with the particular disorder treated. A principal factor in the selection process can be the independent determination of the existence of an established correlation between clinical symptoms of the disease state and increased levels of circulating antibodies to the substance in the victim. Another selection factor is the specific association of the notation of high levels of circulating antibodies thereto. The multiple sclerosis (MS) disease and the treatment thereof according to the invention provides an illustration of application of such selection criteria in determining immunogen components. As previously noted, MS patients inexplicably display a characteristic high level of circulating anti-measles antibodies. MS patients also uniformly possess a lymphocyte-associated antigen which is reactive with certain specific antibodies as described in the diagnostic procedures of U.S. Pat. No. 4,294,818. Both measles virus and the lymphocyte-associated antigen therefor qualify as immunogens "specifically immunologically associated" with the MS disease state which are suitable for combination with histamine in formulation of compositions of the invention useful in alleviating MS disease state symptoms.

The following is a listing of disease states treatable according to the invention and immunogens specifically immunologically associated with the disease state.

| Disease State | Immunogen(s) |
| --- | --- |
| 1. Rheumatoid arthritis | Immunoglobulin G provocative of RF formation |
| 2. Autoimmune hemolytic anemia | Red blood cell surface antigen |
| 3. Glomerulonephritis associated with β hemolytic streptococcal infection | Streptococcal cell surface antigen |
| 4. Myasthenia gravis | Acetylcholine receptor |
| 5. Systemic lupus erythematosis | Human DNA, human epidermal cells, measles virus RNA |
| 6. Pernicious anemia | Intrinsic factor, gastric mucosal cells |
| 7. Hashimoto's thyroiditis | Thyroglobulin |
| 8. Systemic sclerosis (scleroderma) | Human DNA, immunoglobulin G provocative of RF formation |
| 9. Polymyositis | Human myoglobin |
| 10. Sjogren's Syndrome | Thyroglobulin |
| 11. Juvenile diabetes | Beta cells |

Mixtures of the invention are generally administered parenterally (e.g., subcutaneously intramuscularly, sublingually, etc.) although oral administration is contemplated when provision is made to protect the active ingredients from digestive degradation. Subcutaneous administration is preferred, as is sublingual administration. For example, a typical unit dosage form for use in subcutaneous administration would comprise a mixture of a total volume of 0.5 cc of an immunologically acceptable carrier fluid (preferably normal saline) to which has been added a histamine source (preferably as a histamine phosphate solution as previously described) and one or more immunogens (e.g., an inactivated, attenuated measles virus vaccine). A unit dose for sublingual adminstration would provide the same quantity of histamine-and-immunogen-mixture in a single drop (typically 0.05 cc) form.

It is contemplated that varying strengths of the histamine component of the pharmaceutical (biologic) mixtures may be formulated. The attending physician may prescribe, or administer, different levels of histamine reflecting alterations in disease states. This is consistent with the procedure of administration of a "neutralizing" dose which is that concentration which specifically immunosuppresses that part of the patient's prevailing immunological response directed against the agent.

Substantial experience in practice of the invention has revealed that an effective unit dose quantity of histamine for adult patients will be an essentially minute quantity within the range of from about $8.8 \times 10^{-6}$ to about $5.5 \times 10^{-3}$ mg and usually between $4.4 \times 10^{-5}$ and $1.1 \times 10^{-3}$ mg. The quantity of immunogen employed will depend upon the relative purity or homogeneity of the immunogen. As one example, treatment of MS patients according to the present invention has involved use of unit doses containing from $2 \times 10^{-3}$ to $4 \times 10^{-4}$ times the prescribed vaccination dose of attenuated measles virus, vaccine which is generally set at 1000 $TCID_{50}$. Further, a substantial basis exists for believing that the significant, effective immunogenic viral component is a fraction of the virus whose stability is not dependent of the virus being alive at the time of administration. [Indeed, in order to eliminate the potential complicating effects of active measles infection, the virus vaccine preparation employed was allowed to remain at room temperature in phenolated saline over a time of about 3 hours, generally sufficient to kill live virus particles.] Future isolation of the immunologically active, immunogenic fractions(s) of the virus will allow for administration of even smaller weights of substances containing essentially the same quantities of immunogen or synthetic replicas thereof.

As previously noted, administration of histamine and immunogen at separate sites without prior admixture of the components has not proven to have the same effectiveness as a single-site adminstration of mixtures of the components. Thus, while it is possible that beneficial effects may attend parenteral (e.g., subcutaneous) administration of histamine followed by administration of immunogen at the same site (to form a mixture in the patient's skin), such practices are not preferred. The value of admixture of components prior to administrtaton has also been substantiated by the results attending sublingual administration. In treatment of MS patients with histamine and measles virus, it has been generally noted that sublingual adminstration of a given dose is not as effective as the same subcutaneous dose if the mixture administered is only freshly prepared. Effectiveness of sublingual administration is enhanced by the mere expedient of allowing the mixture of components to stand for a period of time prior to administration.

While not intended to be binding with respect to practice of the invention, a hypothesis exists which would explain the basis of these observations. That the administration of the histamine/immunogen mixture is more effective than separate administration of individual components may be the result of the components' forming a highly active complex of two individually less active components. The effectiveness of "fresh" mixtures in subcutaneous administration routes may be the result of an almost immediate complex association of histamine with the immunogen. The observation of increased sublingual effectiveness for mixtures which have stood for extended periods of time (vis-a-vis "fresh" mixtures) may be the result of initial formation of a relatively high molecular weight active complex which is not readily absorbed sublingually, with prolonged standing providing somewhat degraded, lower molecular weight, more easily absorbed, but nontheless active complex.

The following illustrative example relates to practice of the invention in the alleviation of symptoms of multiple sclerosis patients. In the course of the studies set out in the example, it was determined that all multiple sclerosis patients benefitted from administration of admixtures of histamine and immunogen which were within the dose ranges set out above, thereby eliminating the need for individual sensitivity testing carried out in the initial stages of the therapeutic program.

EXAMPLE 1

One hundred and sixty-two patients clinically diagnosed as suffering from multiple sclerosis were treated in a therapeutic program of the invention.

The first 24 of the patients were initiated in a program involving administration of a composition which included three mixture components: (1) histamine phosphate (USP Injection, Eli Lilly); (2) measles virus vaccine (Live, Attenuated, MSD, Attenuvax ®, Merck, Sharp & Dohme); and influenza virus vaccine (Trivalent Types A and B, Wyeth). Employing a progressive series of five-fold dilutions of the components as received from the manufacturers, each patient was skin tested to determine the maximum immunological tolerated intradermal dose of each component. In the case of the measles virus, the commercial vaccine was permitted to stand in phenolated saline at room temperature for 3 hours, an amount of time believed to be sufficient to prompt inactivation of all living virus particles. The three mixture components were then "custom mixed" for each patient to allow for the provision of the indicated dose of each component in the form of 0.5 cc of fluid. Sublingual administration was accommodated by formulation providing the indicated dose in only 0.05 cc of fluid (one drop).

Patients were periodically required to report improvement, worsening or the absence of change with respect to twenty motor, neurologic and psychological difficulties commonly associated with the multiple sclerosis disease state. No report was required if the enumerated difficulty had not been encountered prior to treatment. Patients were also asked to indicate overall improvement, worsening or absence of change with respect to the totality of their disease symptoms.

After about two months of treatment in the program, certain of the patients were switched to treatment with two-component mixtures which included histamine and either measles virus or influenza virus, but not both. Those receiving the measles/histamine combination continued to show improvements on par with those seen with the three-component mixtures, while those receiving the histamine/influenza virus mixture did not. Consequently, except as indicated hereafter, the 24 initial patients and all subsequent multiple sclerosis patients in the program received the two-component, histamine/measles virus, composition.

Certain of the patients were given histamine and measles virus in the form of separate subcutaneous injections at different sites. Upon notation of cessation of alleviation of disease symptoms, these patients were restored to administration of the two components in mixed form.

Certain patients were given two-component mixtures which did not include both histamine and measles. All such mixtures failed to generate improvements in disease symptoms on par with those observed for the combination of measles and histamine and all patients so tested were restored to the measles/histamine combination. The two-component mixtures tested included histamine and either attenuated mumps virus or crude human leukocyte interferon or myelin basic protein (Eli Lilly). Similarly, mixtures of measles virus vaccine and either of two synthetic precursors of histamine (imidazole and imidazole acetate) were not as effective in relieving disease symptoms.

Patients were added to the study over the course of nearly eighteen months, until a total of 166 had been enrolled and received at least some treatments. As of January, 1982, 133 patients remained in the study. Of a total of 29 patients who dropped out of the study, two left before completing two months of treatment or providing any evaluation of treatment effects. Two died of causes unrelated to their multiple sclerosis disease state. Of the twenty-five patients electing to leave the study, only one had reported an overall worsening of symptoms and the remaining 24 reported either no change (16) or an improvement (8).

Table I below tabulates the reports provided by the remaining 133 patients just prior to January, 1982.

TABLE I

| Symptom (Number to Which Applicable) | Length of Time with MS Before Treatment (yrs) | Worse (%) | No Change (%) | Better (%) |
|---|---|---|---|---|
| 1. Strength and Endurance (130) | 0–5 | 9.4 | 28.1 | 62.5 |
|  | 5–10 | 14.3 | 28.6 | 57.1 |
|  | 10+ | 7.9 | 28.6 | 63.5 |
| 2. Energy (132) | 0–5 | 9.1 | 24.2 | 66.7 |
|  | 5–10 | 13.9 | 25.8 | 58.3 |
|  | 10+ | 9.5 | 21.7 | 58.7 |
| 3. Headache (47) | 0–5 | 0.0 | 58.3 | 41.7 |
|  | 5–10 | 23.1 | 23.1 | 53.8 |
|  | 10+ | 9.1 | 36.4 | 54.5 |
| 4. Double Vision (47) | 0–5 | 7.1 | 35.7 | 57.1 |
|  | 5–10 | 5.6 | 33.3 | 61.1 |
|  | 10+ | 0.0 | 50.0 | 50.0 |
| 5. Blurred Vision (64) | 0–5 | 5.0 | 55.0 | 40.0 |
|  | 5–10 | 9.1 | 40.9 | 50.0 |
|  | 10+ | 0.0 | 45.5 | 54.5 |
| 6. Dizziness (56) | 0–5 | 10.5 | 52.6 | 36.8 |
|  | 5–10 | 11.8 | 35.3 | 52.9 |
|  | 10+ | 10.0 | 35.0 | 55.0 |
| 7. Difficulty Swallowing: | 0–5 | 20.0 | 20.0 | 60.0 |

TABLE I-continued

| Symptom (Number to Which Applicable) | Length of Time with MS Before Treatment (yrs) | Worse (%) | No Change (%) | Better (%) |
|---|---|---|---|---|
| Choking (62) | 5–10 | 5.6 | 44.4 | 50.0 |
|  | 10+ | 0.0 | 53.6 | 46.4 |
| 8. Constipation (85) | 0–5 | 0.0 | 52.2 | 47.8 |
|  | 5–10 | 12.0 | 48.0 | 40.0 |
|  | 10+ | 2.7 | 40.5 | 56.8 |
| 9. Bowel Urgency (control) (81) | 0–5 | 5.0 | 40.0 | 55.0 |
|  | 5–10 | 12.5 | 45.8 | 41.7 |
|  | 10+ | 0.0 | 48.6 | 51.4 |
| 10. Bladder Frequency (113) | 0–5 | 7.1 | 39.3 | 53.6 |
|  | 5–10 | 9.7 | 38.7 | 51.6 |
|  | 10+ | 5.6 | 14.8 | 79.6 |
| 11. Bladder Urgency (control) (110) | 0–5 | 7.4 | 37.0 | 55.6 |
|  | 5–10 | 9.7 | 38.7 | 51.6 |
|  | 10+ | 3.8 | 32.7 | 63.5 |
| 12. Sexual Interest and Function (74) | 0–5 | 16.7 | 66.7 | 16.7 |
|  | 5–10 | 18.2 | 63.6 | 18.2 |
|  | 10+ | 2.9 | 79.4 | 17.6 |
| 13. Finger Dexterity; Hand Coordination (110) | 0–5 | 11.5 | 61.5 | 26.9 |
|  | 5–10 | 12.9 | 48.4 | 38.7 |
|  | 10+ | 7.5 | 43.4 | 49.1 |
| 14. Pain - Any Location (64) | 0–5 | 16.7 | 44.4 | 38.9 |
|  | 5–10 | 31.3 | 50.0 | 18.8 |
|  | 10+ | 10.0 | 50.0 | 40.0 |
| 15. Numbness - Any Location (102) | 0–5 | 10.0 | 46.7 | 43.3 |
|  | 5–10 | 8.0 | 56.0 | 36.0 |
|  | 10+ | 8.5 | 57.4 | 34.0 |
| 16. Depression (77) | 0–5 | 9.5 | 52.4 | 38.1 |
|  | 5–10 | 23.1 | 34.6 | 42.3 |
|  | 10+ | 3.3 | 33.3 | 63.3 |
| 17. Balance (123) | 0–5 | 15.6 | 46.9 | 37.5 |
|  | 5–10 | 29.4 | 41.2 | 29.4 |
|  | 10+ | 10.5 | 52.6 | 36.8 |
| 18. Walking (109) | 0–5 | 23.1 | 50.0 | 26.9 |
|  | 5–10 | 19.4 | 58.1 | 22.6 |
|  | 10+ | 13.5 | 55.8 | [30.6] |
| 19. Speech (71) | 0–5 | 17.6 | 41.2 | [41.2] |
|  | 5–10 | 18.2 | 40.9 | [40.9] |
|  | 10+ | 6.5 | 41.9 | [51.6] |
| 20. Spasms or Tremors (101) | 0–5 | 20.0 | 20.0 | 60.0 |
|  | 5–10 | 16.7 | 26.7 | 56.7 |
|  | 10+ | 15.7 | 39.2 | 45.1 |
| 21. Overall Response 128* | 0–5 | 9.1 | 18.2 | [72.7] |
|  | 5–10 | 5.9 | 17.6 | [76.5] |
|  | 10+ | 4.9 | 21.3 | [73.8] |

*5 patients did not respond.

Table II below provides an analysis of the number of unit doses administered in the course of therapy. All patients were initiated in a subcutaneous injection program. Some were changed to either drops alone or a combination of shots and drops. A total of 45 of the 111 patients who tried the sublingual drops at one time in the program did not return to the subcutaneous injection regimen.

TABLE II

| Route of Administration | Total Patients | Less Than 1 per 2 days (%) | 1 per 2 days (%) | 1 Daily (%) | 2 Daily (%) | 3 Daily (%) | More Than 3 Daily (%) |
|---|---|---|---|---|---|---|---|
| Injection | 133 | 4.5 | 11.2 | 53.7 | 26.8 | 3.7 | 0.0 |
| Drop (only) | 47 | 0.0 | 2.1 | 17.0 | 48.9 | 23.4 | 8.5 |
| Mixed Shot/Drop | 23 | 0.0 | 0.0 | 48.0 | 52.0 | 0.0 | 0.0 |

The following example illustrates practice of the invention in treatment of rheumatoid arthritis disease symptoms. As in the previous example, it was determined that for all patients the neutralizing levels of the histamine admixture component fell within the concentration levels previously described.

EXAMPLE 2

Six patients clincially diagnosed as suffering from rheumatoid arthritis were initiated in a therapeutic program according to the invention. Each patient was tested to determine the maximum immunologically tolerated intradermal dose of (1) histamine phosphate (USP Injection, Eli Lilly); (2) measles virus vaccine (Live, Attenuated, MSD, Attenuvax ®, Merck, Sharp & Dohme); and (3) rheumatoid factor-provoking, rabbit anti-sheep red blood cell IgG (Cappel Labs). Based on test results, compositions were formulated by admixture of the three components so as to provide the indicated amount of each component in either a 0.5 cc subcutaneously injectable fluid form or a 0.05 cc fluid droplet form for sublingual administration. The frequency of administration varied from one injection every two days to two injections per day, or 1 to 2 sublingual droplet adminstrations per day. After 6 months of treatment, all six patients have reported improvement in terms of: (1) decreased pain; (2) increased mobility and flexibility; (3) decreased swelling; (4) decreased inflammation; and (5) increased energy. Certain of the patients were subsequently changed over to a regimen wherein a histamine/IgG mixture (without measles virus) was administered and all these continued to show improvement, indicating that the measles virus component is not essential for rheumatoid arthritis treatment.

Favorable responses were noted for use of admixtures including from 0.1 to 0.005 mg of chromatographically pure IgG was employed. Preliminary data indicates that human IgG is as effective as the above-noted IgG of rabbit origin.

Examples 1 and 2 are believed to illustrate the applicability of the present invention to treatment of a variety of disease states other than multiple sclerosis and rheumatoid arthritis. Indeed each of the ten additional specific states of an "autoimmune" character previously enumerated as well as other immune disorders are believed to be treatable with similar good results by administration of effective amounts of admixture compositions consisting of histamine and one or more listed immunogens which are specifically immunologically associated with the disease state.

The following example relates to practice of the invention in alleviation of the symptoms of disease states which are not classically described as involving an immune component.

EXAMPLE 3

Fifteen human patients experiencing chronic pain (i.e., pain without substanital remission over a period of three months or more) were initiated in a therapeutic program. Five of the patients had previously been diagnosed as having osteoarthritis and the remaining ten had initially experienced pain subsequent to severe physical trauma. Each patient was tested to determine the maximum tolerated intradermal dose of histamine phosphate and inactivated attenuated measles virus vaccine as in the preceding examples. In each instance, the histamine admixture component concentration determined was in the range of from $8.8 \times 10^{-6}$ to $5.5 \times 10^{-3}$ mg of histamine phosphate per dose and the measles admixture component dose concentration was in the range of $2 \times 10^{-3}$ to $4 \times 10^{-4}$ times the prescribed vaccination dose of virus. The frequency of administration varied from one injection every 4 days to two injections per day, and/or 1 to 3 sublingual drops per day. All patients experienced remission of pain, with the onset of remission occurring in some cases as soon as a few hours after the first administration of the composition.

Two human patients suffering from recurrent herpes simplex virus type II infections were skin tested to determine maximum tolerated intradermal doses of histamine phosphate, measles virus vaccine and influenza virus vaccine in the manner of the previous examples. Unit dose concentrations for histamine phosphate and for each of the virus preparations were within the ranges described above. Both patients received subcutaneous injections of the three-component mixture compositions on a daily basis and reported immediate remission of lesion pain, followed by decrease in size and eventual elimination of lesions within 2 to 3 days.

A total of ten horses exhibiting moderate to severe lameness were skin tested with histamine phosphate and measles virus vaccine. Each was then treated with a mixture of the indicated quantities which were in the ranges previously noted. Rapid recovery was observed in all animals and all have remained symptom-free upon continuation of treatment on regimens varying from 1 injection per day to 1 injection per week.

Numerous modifications and variations of the invention as described in the above illustrative examples are expected to occur to those skilled in the art. Consequently, only such limitations as appear in the appended claims should be placed thereon.

What is claimed is:

1. A method for alleviating chronic pain symptoms comprising administering to the disease victim an effective amount of a composition comprising a mixture of histamine and inactivated, attenuated measles virus or an immunologically active fraction thereof.

2. The method of claim 1 wherein histamine is administered in the form of a water soluble histamine salt.

3. The method of claim 1 wherein said composition comprises in unit dosage form, from about $8.8 \times 10^{-6}$ to about $5.5 \times 10^{-3}$ mg of histamine phosphate.

4. The method of claim 1 wherein the measles virus is an inactivated, attenuated vaccine strain.

5. The method of claim 1 wherein said composition comprises, in unit dosage form, from about $2 \times 10^{-3}$ to about $4 \times 10^{-4}$ times the prescribed vaccination dose of an inactivated, attenuated measles virus vaccine strain.

6. The method of claim 1 wherein said composition is administered parenterally.

7. The method of claim 6 wherein said composition is administered subcutaneously or sublingually.

* * * * *